(12) United States Patent
Metala et al.

(10) Patent No.: US 7,903,140 B2
(45) Date of Patent: Mar. 8, 2011

(54) ILLUMINATED INSPECTION APPARATUS AND METHOD OF EMPLOYING THE SAME

(75) Inventors: Michael J. Metala, Murrysville, PA (US); James Bauer, Gibsonia, PA (US); John E. Noll, Port Vue, PA (US)

(73) Assignee: Siemens Energy, Inc., Orlando, FL (US)

( * ) Notice: Subject to any disclaimer, the term of this patent is extended or adjusted under 35 U.S.C. 154(b) by 1652 days.

(21) Appl. No.: 11/169,479

(22) Filed: Jun. 29, 2005

(65) Prior Publication Data

US 2007/0002133 A1 Jan. 4, 2007

(51) Int. Cl.
*H04N 7/18* (2006.01)
*F21V 33/00* (2006.01)

(52) U.S. Cl. .......................................... 348/61; 362/184

(58) Field of Classification Search .................... 348/61, 348/143, 148; 362/184, 205, 231, 234, 203, 362/253, 190, 191, 259, 800; 396/155, 429
See application file for complete search history.

(56) References Cited

U.S. PATENT DOCUMENTS

| | | | |
|---|---|---|---|
| 6,095,661 A * | 8/2000 | Lebens et al. ................. | 362/184 |
| 6,877,878 B2 | 4/2005 | Raskas | |
| 6,880,951 B2 | 4/2005 | Yoon | |
| 6,890,086 B2 | 5/2005 | Shiu | |
| 6,893,140 B2 | 5/2005 | Storey et al. | |
| 7,568,816 B2 * | 8/2009 | Brass et al. ................... | 362/231 |
| 7,784,963 B2 * | 8/2010 | Galli et al. ................... | 362/184 |
| 2004/0201989 A1 * | 10/2004 | Raskas .......................... | 362/253 |
| 2006/0028811 A1 * | 2/2006 | Ross et al. .................... | 362/157 |
| 2006/0125918 A1 * | 6/2006 | Sutton .......................... | 348/148 |
| 2006/0171700 A1 * | 8/2006 | Yang et al. .................... | 396/155 |
| 2007/0098391 A1 * | 5/2007 | Howard et al. ............... | 396/155 |

OTHER PUBLICATIONS

"LED Flashlight includes camera and night vision system, Otter Tail Power Co."; [online]; [retrieved on Sep. 6, 2005]; Retrieved from http://news.thomasnet.com/fullstory/459696, pp. 1-4.

"MII Flashcam—Tactical Flashlight with built in Video Recorder, night vision, monitor, and . . . "; [online]; retrieved on Sep. 6, 2005]; Retrieved from http://www.miiflashcam.com/, pp. 1-3.

* cited by examiner

*Primary Examiner* — Behrooz Senfi

(57) ABSTRACT

An inspection system (200) is for inspecting power generation equipment (202) and includes a remote receiving device (134) which receives images captured and transmitted by an inspection apparatus (100). A recording device (142) records the images thereby providing a permanent record of the inspection. The inspection apparatus (100) comprises: a flashlight assembly (102) including a power supply (110), an elongated housing (104) having first and second ends (105, 107), a lens body (120) coupled to the first end (105), and a lens cover (114) covering the lens body (120). The inspection apparatus (100) further includes an imaging system (122) having a camera (130), such as a wireless video camera, which is disposed within the lens body opening (121), an illumination assembly (106) which generally surrounds the camera (130), and a protective cover (116) for the illumination assembly (106). An associated method is also disclosed.

20 Claims, 3 Drawing Sheets

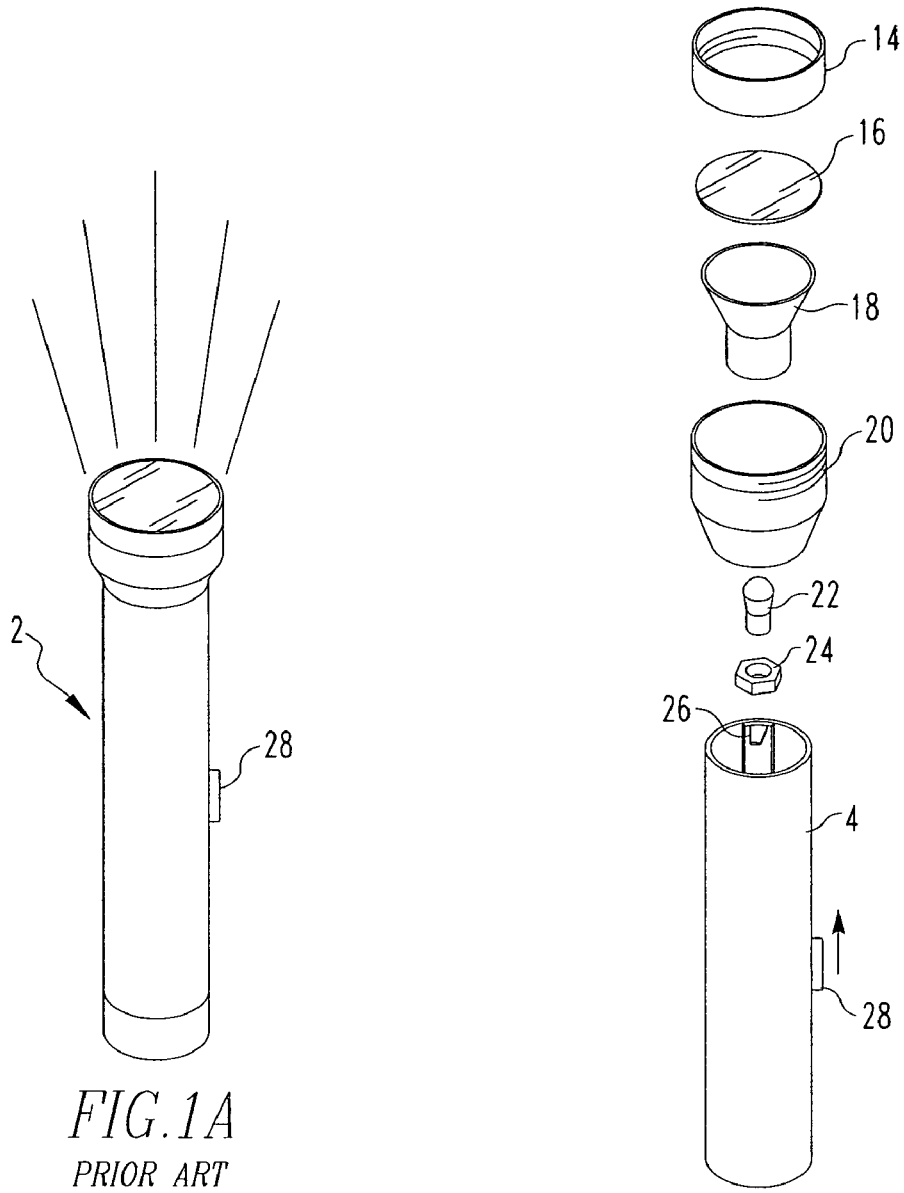
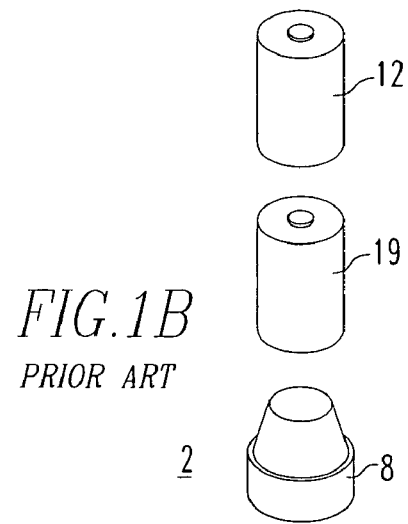
FIG.1A
PRIOR ART
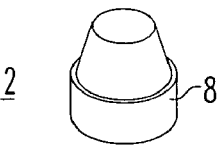
FIG.1B
PRIOR ART

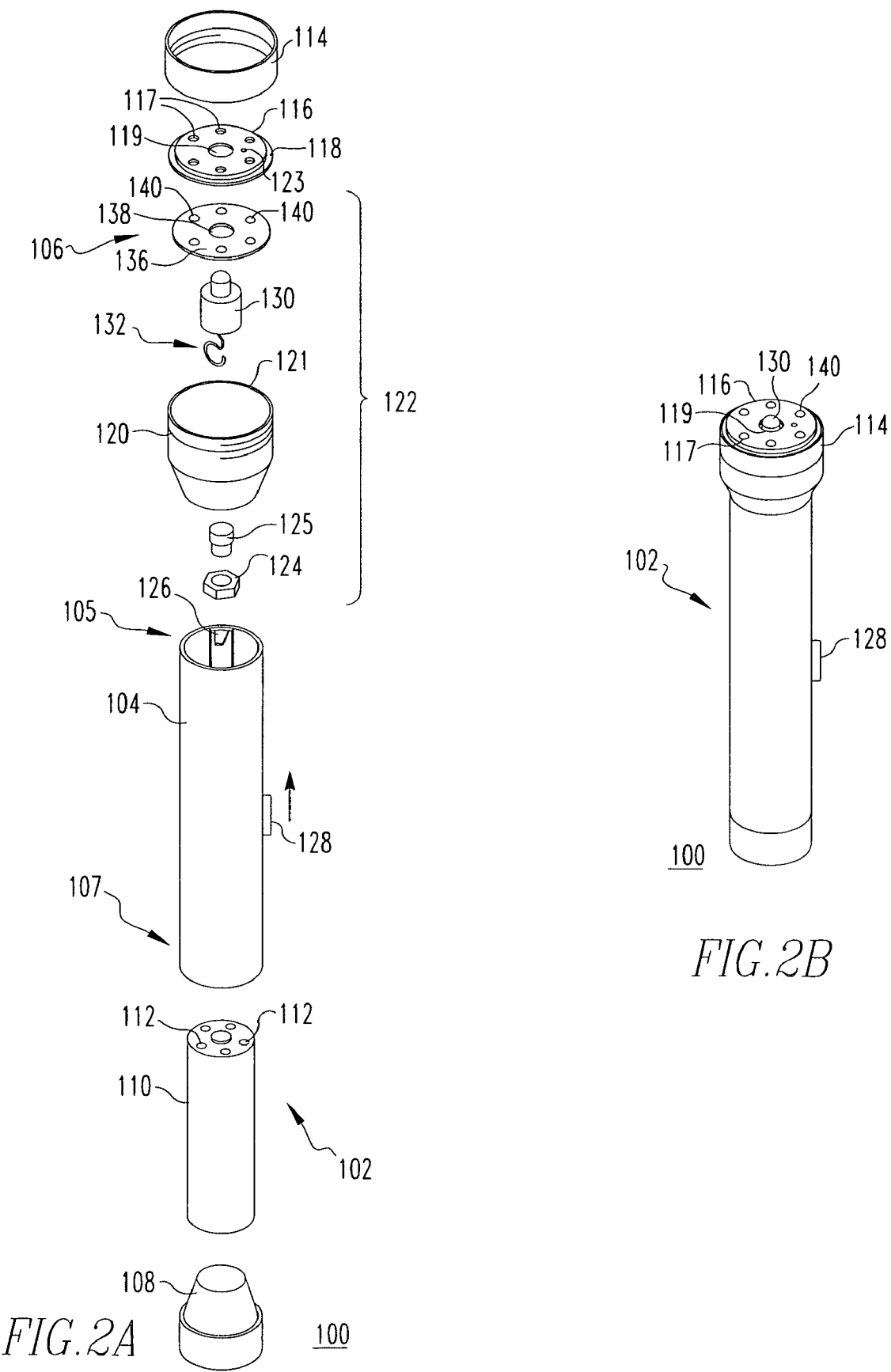

ILLUMINATED INSPECTION APPARATUS AND METHOD OF EMPLOYING THE SAME

BACKGROUND OF THE INVENTION

1. Field of the Invention

The present invention relates generally to power generation equipment and, more particularly, to an illuminated inspection apparatus for inspecting power generation equipment. The invention also relates to a method of employing an illuminated inspection apparatus.

2. Background Information

Power generation equipment manufacturers and service suppliers frequently provide on-site repair, modifications, and maintenance of the equipment (e.g., without limitation, turbine generators; electrical generators; combustion turbines) that they manufacture and install at utility sites in the global market. After performing work on power generation equipment at a utility site and before the equipment can be brought back online by the utility, an inspection is typically required in order to, for example, assure that no foreign objects are present.

By way of example, without limitation, the electric generator at most utility sites is serviced under known foreign material exclusion (FME) rules and procedures. FME rules involve inventorying all items which are taken into the generator before and after the work is performed because leaving a wrench, hammer or other tool, or even a rag, for example, could result in a serious and costly equipment failure.

Often, after the generator is reassembled, an inspector enters through a manway opening and performs a crawl-through visual inspection of the generator. The inspector typically uses a flashlight and roams through the small access areas of the generator stator looking for any unaccounted for items. Specifically, the inspector shines the flashlight at the accessible locations and visually looks for foreign objects. Following the inspection, the inspector re-emerges from the generator and provides the customer with a report. Thus, a conventional inspection entails an inspector, typically of relatively small physical stature, crawling through a contoured space and visually examining the generator with a flashlight. Although the inspector may take written notes, only the inspector sees what she is viewing and no permanent record or physical evidence is available for reconsideration and, in some instances, multiple crawl-through inspections are made by multiple individuals to confirm that nothing was missed during inspection.

In some cases, a remote videoprobe has been employed in an attempt to improve upon the manual crawl-through inspections. The remote videoprobe is inserted into the generator and viewed, for example, from a monitor at a location separate for the generator. However, this offers only a limited inspection and limited view of the generator internals. Therefore, a crawl-through inspection is typically still required.

As previously noted, a flashlight is typically used to illuminate the interior of the generator during the inspection. Flashlights 2 are well known in the art and, as shown in FIGS. 1A and 1B, generally comprise an elongated battery housing 4 with an illuminating assembly 6 at one end and a cap 8 at the opposing end. The battery housing 4 encloses a number of batteries, such as the two D-cell batteries 10, 12 shown in FIG. 1B. The cap 8 is typically threaded to secure the batteries 10, 12 within the housing 4. At the opposite end, the flashlight 2 usually includes a threaded lens cover 14 structured to secure the illuminating assembly 6 together.

The illuminating assembly 6, in addition to the lens cover 14, includes a lens 16, a reflector 18, a lens body 20, and a bulb 22. The bulb 22 is generally disposed within the lens body 20 and coupled to the housing 4 by a fastener, such as the nut 24, shown in FIG. 1B. The bulb 22 protrudes through the reflector 18 which is made from a highly reflective material, such as aluminum, in order to reflect and thus enhance the light emitted from the bulb 22. The lens 16 covers the reflector 18 and bulb 22 therein and is secured in place by the lens cover 16. The bulb 22 is illuminated by bringing the batteries 10, 12 into electrical communication with an electrical conductor 26 coupled to the bulb 22. Thus, the flashlight 2 may be turned on by achieving such electrical communication which may be accomplished, for example by twisting the cap 8 with respect to the body 4 or by actuating a switch 28 to an "ON" position (FIG. 1A).

In view of the foregoing, there is a need for an improved apparatus and method for inspecting power generation equipment.

There is a further need for an inspection apparatus and method which provides an accurate and permanent record of the inspection.

There is, therefore, room for improvement in inspection apparatus and in methods of employing inspecting apparatus.

SUMMARY OF THE INVENTION

These needs and others are satisfied by the present invention, which provides an inspection apparatus, system, and method for conducting an accurate inspection of, for example, power generation equipment while permitting remote, real-time or delayed viewing of the inspection and the generation of a permanent record of the inspection. By modifying a conventional flashlight assembly, in at least one embodiment of the invention, to include, among other features, a wireless video camera and transmitter, the present invention provides an economical inspection apparatus and method for transmitting images acquired, for example, during a crawl-through inspection of a turbine generator. The invention thus enables the images to be viewed and recorded at a remote location (e.g. outside of the generator), substantially overcoming known disadvantages associated with the prior art, including the need for repetitive inspections and the inaccurate and/or incomplete nature of inspector reports.

As one aspect of the invention, an inspection apparatus comprises: a flashlight assembly including a power supply, an elongated housing having a first end and a second end, a lens body coupled to the first end, and a lens cover covering the lens body, the lens body including an opening; an imaging system including a camera disposed within the opening of the lens body; an illumination assembly generally surrounding the camera; and a protective cover securing the illumination assembly to the first end of the housing. The camera may be a wireless video camera wherein the imaging system comprises the wireless video camera and a transmitter, such as a radio frequency (RF) transmitter, which transmits images captured by the wireless camera to a remote receiving device, such as a RF receiver.

The illumination assembly may comprise: a printed circuit board coupled to the reflector and including an aperture, the camera being disposed within the aperture; and at least one light source disposed on the printed circuit board adjacent the camera. The printed circuit board may be generally circular and the at least one light source may include a plurality of light emitting diodes disposed around the perimeter of the generally circular printed circuit board in order to form an illuminable ring substantially surrounding the camera.

The flashlight assembly may further include an electrical conductor and a switching apparatus, the electrical conductor being in electrical communication with the imaging system and the illumination assembly, the switching apparatus being operable between an ON position in which the electrical conductor is electrically, conductively connected to the power supply in order to provide power to the imaging system and the illumination assembly, and an OFF position in which the electrical conductor is not in electrical communication with the power supply.

As another aspect of the invention, an inspection system for inspecting power generation equipment comprises: a remote receiving device adapted to receive images captured during inspection of the power generation equipment; a recording device structured to record the images; and an inspection apparatus for capturing the images, the inspection apparatus comprising: a flashlight assembly including a power supply, an elongated housing having a first end and a second end, a lens body coupled to the first end, and a lens cover covering the lens body, the lens body including an opening; an imaging system including a camera disposed within the opening of the lens body; an illumination assembly generally surrounding the camera; and a protective cover securing the illumination assembly to the first end of the housing.

The imaging system may include a display being in electrical communication with a remote receiving device in order to display the images captured by the wireless video camera, and a recording device for recording the images.

As another aspect of the invention, a method of inspecting power generation equipment comprises: adapting a conventional flashlight to provide an inspection apparatus which comprises: a power supply, an elongated housing having a first end and a second end, a lens body coupled to the first end, a lens cover covering the lens body, the lens body including an opening, an imaging system including a camera disposed within the opening of the lens body, an illumination assembly generally surrounding the camera, a protective cover securing the illumination assembly to the first end of the housing, and an electrical conductor with a switching apparatus, the electrical conductor being in electrical communication with the imaging system and the illumination assembly, the switching apparatus being operable between an ON position in which the electrical conductor is electrically, conductively connected to the power supply in order to provide power to the imaging system and the illumination assembly, and an OFF position in which the electrical conductor is not in electrical communication with the power supply.

The method may further include one or more of the steps of turning the inspection apparatus ON in order to illuminate the illumination assembly and to begin capturing images, conducting an inspection of the power generation equipment, displaying the images captured by the wireless video camera during the inspection on a display, and recording the images using a recording device.

BRIEF DESCRIPTION OF THE DRAWINGS

A full understanding of the invention can be gained from the following description of the preferred embodiments when read in conjunction with the accompanying drawings in which:

FIG. 1A is a perspective view of a prior art flashlight shown in the ON position;

FIG. 1B is an exploded, isometric view of the flashlight of FIG. 1A;

FIG. 2A is an exploded, isometric view of a flashlight assembly modified to provide an inspection apparatus in accordance with the present invention;

FIG. 2B is an assembled view of the inspection apparatus of FIG. 2A; and

DESCRIPTION OF THE PREFERRED EMBODIMENTS

Figure 3:
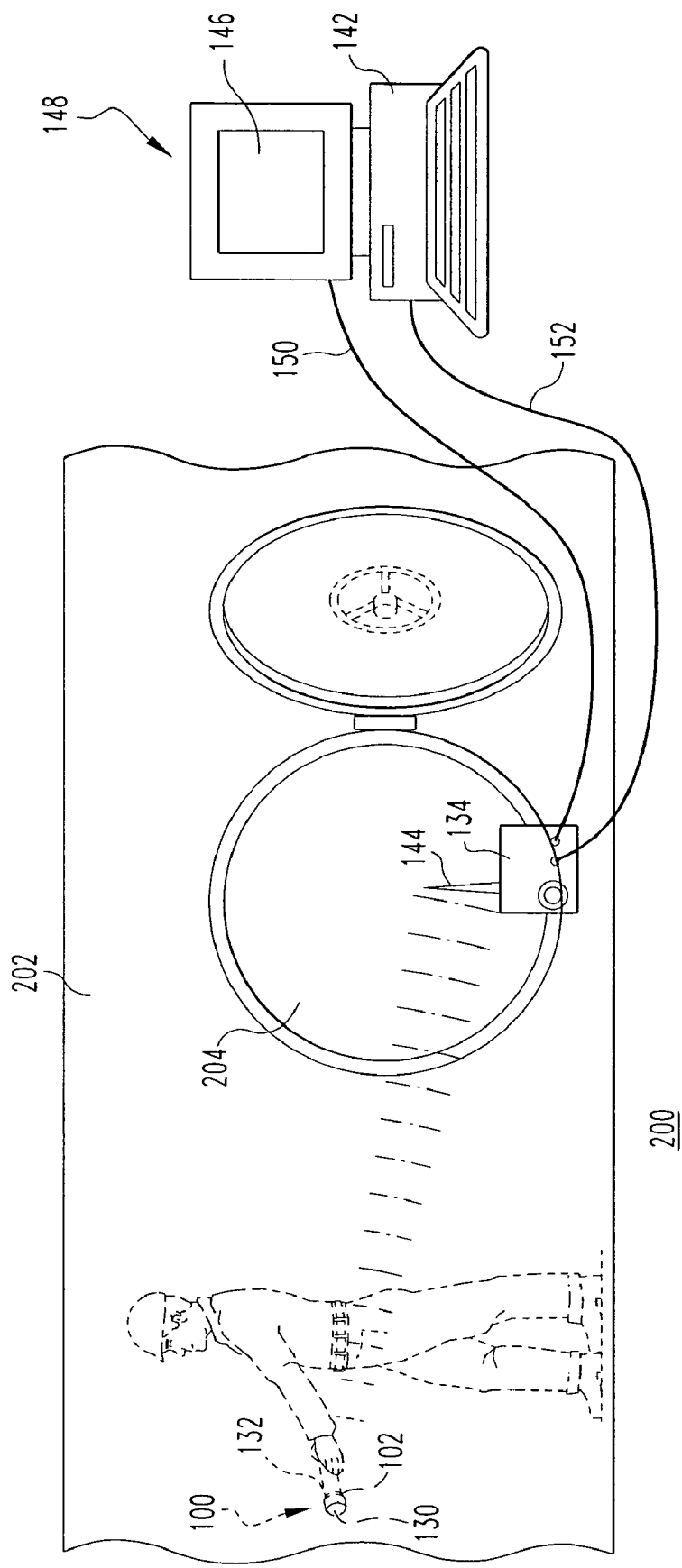
FIG. 3 is a schematic view of an inspection system and method of inspecting power generation equipment using the inspection apparatus of FIG. 2B in accordance with the invention.

The invention will be described as applied to the inspection of power generation components (e.g., without limitation, steam turbines, combustion turbines, electrical generators and other components at power plants and other utility sites), although it will become apparent that it could also be applied to the inspection of any component in any industry as well as, for example, without limitation, as a security tool for law enforcement (e.g. without limitation, for conducting and recording bomb searches).

Directional phrases used herein, such as, for example, upper, lower, top, bottom, left, right, and derivatives thereof, relate to the orientation of the elements shown in the drawings and are not limiting upon the claims unless expressly recited therein.

As employed herein, the statement that two or more parts are "coupled" together shall mean that the parts are joined together either directly or joined through one or more intermediate parts.

As employed herein, the term "number" shall refer to one and more than one (i.e. a plurality).

As employed herein, the term "wireless" shall expressly include, but not be limited by, radio frequency (RF), infrared, wireless area networks, IEEE 802.11 (e.g., 802.11a; 802.11b; 802.11g), IEEE 802.15 (e.g., 802.15.1; 802.15.3, 802.15.4), other wireless communication standards, DECT, PWT, pager, PCS. Wi-Fi, Bluetooth™, and cellular.

Referring now to the figures and, in particular to FIGS. 2A and 2B, an inspection apparatus 100 in accordance with the invention, is shown. The inspection apparatus 100 generally comprises a flashlight assembly 102 including a power supply 110, an elongated housing 104 having a first end 105 and a second end 107, a lens body 120 coupled to the first end, and a lens cover 114 covering the lens body, as shown in FIG. 2B. The lens body 120 includes an opening 121 extending therethrough. An imaging system 122 including a camera 130 is disposed within the opening 121. An illumination assembly 106 generally surrounds the camera 130. A protective cover 116 generally overlies and thus protects the illumination assembly 106.

It will be appreciated that, in one embodiment of the invention, the inspection apparatus 100 can be created by modifying an existing flashlight (e.g., without limitation, flashlight 2 of FIGS. 1A and 1B), thereby providing a relatively simple, quick and economical method and apparatus for improving crawl-through inspections of power generation equipment 200 (FIG. 3), for example.

Comparing the known flashlight 2 of FIG. 1B with the flashlight assembly 102 of the exemplary apparatus 100, shown in FIG. 2A, it will be understood that the primary modification or difference between the inspection apparatus 100 of the invention and the prior art flashlight 2 is the addition of an imaging system, generally indicated by reference 122 of FIG. 2A. Specifically, the conventional light source of the flashlight, which in the example of FIG. 1B is an incandescent light bulb 22, is replaced with a camera 130. The exemplary camera 130 is a wireless video camera including a radio frequency (RF) transmitter 132 for transmitting images captured during the inspection to an exemplary RF receiver 134 (FIG. 3) or other suitable receiving device which can be disposed at a location remote from the inspection. For example, as will be discussed in further detail hereinbelow, the receiver 134 can be disposed outside of the power generation equipment 202 in order to receive images captured by the inspection apparatus 100 during a crawl-through inspection within the equipment 202, as shown in FIG. 3.

It will be appreciated that any suitable camera or other imaging system could be employed without departing from the scope of the present inventions. For example, the camera could be a conventional snap-shot camera or a digital camera having a triggering mechanism (not shown) for the inspector to periodically take pictures during the inspection, thus creating a permanent record of the inspection. The camera could also comprise, for example, thermal imaging or infrared equipment for taking corresponding measurements and readings during an inspection.

Continuing to refer to FIG. 2A, the illumination assembly 106 of the inspection apparatus 100 includes a printed circuit board 136 (PCB) disposed in the lens body 120, as shown. As shown, the exemplary PCB 136 is generally circular in shape and the exemplary wireless video camera 130 is disposed within an aperture 138 through the center of the PCB 136.

The illumination assembly 106 includes at least one light source 140 disposed adjacent the camera 130. The light source 140, which may be any known or suitable illumination source, functions to provide light for an inspector in much the same way the conventional flashlight of FIG. 1A emits light. However, it also functions to provide an appropriate light source for the exemplary wireless video camera 130 to capture pictures. The at least one light source 140 in the example of FIG. 2A is a plurality of light emitting diodes (LED) disposed around the perimeter of the exemplary generally circular PCB 136, as shown. In this manner, an illuminable ring substantially surrounds the wireless video camera 130.

The protective cover 116 generally overlies and protects the illumination assembly 106. Thus, when assembled, as shown in FIG. 2B, the exemplary illumination assembly 106 and imaging system 122 are coupled to the first end 105 of the flashlight assembly housing 104 in the following sequence. First, the lens body 120 is coupled to the first end 105 by way of any known or suitable fastening mechanism. For example, the lens body 120 and the first end 105 could be threaded to include corresponding male and female threads, respectively, or, as in the example of FIG. 2A, the lens body 120 could be connected by way of a nut 124 and connector 125 which are coupled to an exemplary electrical conductor 126 (discussed in further detail hereinbelow). The wireless video camera 130 is then received within the opening 121 of the lens body 120 and the exemplary generally circular PCB 136 is inserted into the lens body 120 over the camera 130 such that the camera 130 is disposed within the aperture 138 of the printed circuit board 136. Next, the protective cover 116 is placed over the illumination assembly 106 such that it substantially covers the LEDs 140 thereof In the example of FIGS. 2A and 2B the LEDs 140 are received in openings 117 in the protective cover 116 and the camera 130 is received through a center hole 119. The protective cover 116 also includes another hole 123 for receiving, for example, the antenna of the exemplary RF transmitter 132. However, other suitable configurations are within the scope of the invention. It will also be appreciated that although the exemplary protective cover 116 is contemplated as being made from a clear plastic material, such as PLEXIGLASS, any known or suitable material could be used. Finally, the lens cover 114 is attached over the protective cover 116 and engages a lip 118 thereof in order to secure it, the illumination assembly 106, and the imaging system 122 to the lens body 120. In the example of FIG. 2A, this is accomplished again by corresponding male and female threads on the lens cover 114 and the outer perimeter of the lens body 120, respectively. When assembled, the illumination assembly 106 and the imaging system 122 are in electrical communication with the electrical conductor 126. Thus, when the power supply 110 is electrically, conductively connected to the electrical conductor 126, it energizes both the camera 130 and the exemplary LEDs 140.

More specifically, the flashlight assembly 102 further includes a switching apparatus 128 which is operable between an ON position in which the electrical conductor 126 is electrically, conductively connected to the power supply 110 in order to provide power to imaging system 122 and the illumination assembly 106 and, an OFF position in which the electrical conductor 126 is not in electrical communication with the power supply 110. In the example shown and described herein, the switching apparatus 128 is a conventional slide-type switch disposed on the side of the flashlight assembly housing 104. Such a switch 128 is simply actuated between an upward (from the prospective of FIGS. 2A and 2B) position corresponding to the ON position, and a downward (from the prospective of FIGS. 2A and 2B) position corresponding to the OFF position. It will, however, be appreciated that any known or suitable alternative switching apparatus, such as, for example, a push button (not shown), could be employed. Alternatively, the switching apparatus or mechanism for turning the inspection apparatus 1000N could involve merely twisting the lens body 120 or the cap 108 at the second end 107 of the housing 104 in order to bring the electrical conductor 126 into contact with the power supply 110.

It will also be appreciated that the power supply 110 may comprise any known or suitable power source. For instance, in the example of FIG. 1B, the power supply comprises 2D-cell batteries aligned in parallel within the battery housing 4 and secured together therein by the cap 8. In the example of FIG. 2A, a battery assembly 110 is employed which comprises a plurality of smaller batteries such as those which are commercially available under the designation of "AA". Six AA batteries 112 are employed in the exemplary battery assembly 110 power supply of the exemplary inspection apparatus 100. This enables the inspection apparatus 100 to be powered without requiring a physical connection (e.g. wire) to a separate power source (not shown). However, it will appreciated that the inspection apparatus 100 could be configured to be connected, for example, by way of a cable (not shown) to a separate power source such as a generator (not shown), without departing from the scope of the present invention. It will further be appreciated that any known or suitable alternative configuration of battery assembly or other suitable power supply could be employed. For example, the flashlight assembly 102 may be designed to be rechargeable, with the cap 108 and housing 104 comprising a single, unitary component.

It will still further be appreciated that, although the inspection apparatus 100 has been described and illustrated herein as comprising a modified conventional flashlight (e.g., flashlight 2 of FIGS. 1A and 1B), the apparatus 100 could alternatively comprise an assembly 102 which is entirely new, so as not to use any components from an existing flashlight. In this manner, various parts of the apparatus 100 such as, for example, the lens body 120 and housing 104, could be modified to have any desired alternative shape and configuration. For example, the lens body 120 and housing 104 could be molded as one single-piece.

FIG. 3 shows an inspection system 200 where the inspection apparatus 100 is employed to capture images during a crawl-through inspection of power generation equipment, such as a turbine generator 202. It will, however, as previously discussed, be appreciated that the inspection apparatus 100 could be employed, individually or as part of the inspection assembly 200, in a variety of alternative applications other than with respect to inspecting power generation equipment 202.

The inspection system 200 in the example of FIG. 3 includes the remote receiving device 134 which, as previously discussed is a RF receiver in the present example. The RF receiver is adapted to receive the images captured by the exemplary wireless video camera 130 and transmitted by the RF transmitter 132 thereof. The exemplary RF receiver 134 includes an antenna 144 which, as is known in the art, assists in receiving the radio signals transmitted by the transmitter 132. Accordingly, it will be appreciated that the inspection apparatus 100, in the present example, is completely wireless with respect to the remainder of the inspection system 200. This is advantageous in that it enables the inspector to move freely during the inspection without having to worry about tangled wires or insufficient wire or cable length between the inspection apparatus 100 and other components of the inspection system 200. It will be understood, however, that the inspection apparatus 100 in other embodiments of the invention could in fact be connected to various inspection system components, such as the receiver 134 by one or more wires (not shown) in applications where the advantages of wireless technology are not essential.

As previously discussed, it is desirable to create a permanent record of the inspection. Accordingly, the inspection system 200 of the present invention further includes a recording device 142 for recording the images or video footage transmitted from the inspection apparatus 100. The recording device 142 may include any known or suitable memory which may be any of a variety of internal and/or external storage media including, without limitation, RAM, ROM, EPROM, EEPROM, and/or the like. The recording device 142 could be located within the flashlight assembly 102 of the inspection apparatus 100 itself or, as in the example of FIG. 3, the recording device 142 could be separate from the inspection apparatus 100 (e.g., without limitation, a computer hard drive). The exemplary recording device 142 is connected to the receiver 134 by way of a cable 152 in order to receive and record the inspection images as they are transmitted from the inspection apparatus 100. In this manner, a permanent record of the inspection is created. The inspection can, therefore, be replayed at a subsequent point in time in order to, for example, confirm that no foreign objects were found within the turbine generator 202 during the crawl-through inspection after maintenance or repair of the generator 202.

Continuing to refer to FIG. 3, the exemplary inspection system 200 further includes a display 146 which is in electrical communication with the receiver 134 by way of a cable 150. The display 146 which, in the example of FIG. 3, is a computer monitor 148, displays the images captured by the inspection apparatus 100 as they are received by the receiver 134. In this manner, the inspection may be viewed in real-time. This is advantageous in that the customer, for example, by actually monitoring the inspection as it occurs, can be confident to immediately return the equipment 202 to service following completion of the inspection. Watching the inspection on the monitor 148 as it occurs also provides the ability to direct or otherwise provide instructions to the inspector during the inspection rather than having to perform multiple inspections, for example, when an item or portion of the equipment is overlooked. Communication to the inspector from the individual reviewing the inspection on the monitor 148 at a remote location can be achieved by any known or suitable communication mechanism, such as a walkie-talkee, a cellular phone, or a short range radio (not shown). Communications can also be made and the inspection may be broadcast or otherwise transferred via the internet.

It will also be appreciated that the inspection apparatus 100 could alternatively be employed, for example, with a remote control device which could be directed to perform the inspection, thereby replacing the need for a human inspector. In the example of FIG. 3, an inspector is shown conducting an inspection within an interior portion of a turbine generator 202 after having entered the generator 202 by way of a manway 204. The exemplary RF receiver 134 is disposed approximately manway 204 in order to provide the most direct path for radio signals (indicated generally by the dashed line of FIG. 3) transmitted from the inspection apparatus transmitter 132 thus providing the clearest possible reception for display of the inspection images on the monitor 148.

Accordingly, the present invention provides an apparatus and method for remotely viewing and/or creating a permanent record of an inspection which is conducted using a relatively simple and economical wireless inspection apparatus 100. The inspection apparatus 100 can comprise a flashlight assembly modified to include a wireless video camera 134 and appropriate illumination assembly 106. The invention thus provides quality images without requiring complex equipment (e.g., without limitation, a view finder). The inspector conducts the inspection in a conventional manner, using the inspection apparatus 100 as an illumination device while it simultaneously captures images and transmits them for remote viewing and/or the creation of a permanent record of the inspection.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof.

What is claimed is:

1. An inspection apparatus comprising:
    a flashlight assembly including a power supply, an elongated housing having a first end and a second end, a lens body coupled to the first end, and a lens cover covering said lens body, said lens body including an opening;
    an imaging system including a camera disposed within the opening of said lens body;
    an illumination assembly generally surrounding said camera said illumination assembly comprising a plurality of light sources; and
    a protective cover structured to at least partially overlay and to protect said illumination assembly, said protective cover including a center hole and a plurality of openings disposed around said center hole,
    wherein said camera extends through said center hole of said protective cover; and
    wherein each of said light sources extends through a corresponding one of said openings of said protective cover.

2. The inspection apparatus of claim 1 wherein said camera is a wireless video camera.

3. The inspection apparatus of claim 2 wherein said imaging system comprises said wireless video camera and a transmitter which is adapted to transmit images captured by said wireless camera to a remote receiving device.

4. The inspection apparatus of claim 1 wherein said illumination assembly further comprises:
  a reflector disposed within said lens body;
  a printed circuit board coupled to said reflector and including an aperture, said camera being disposed within the aperture; and
  said light sources being disposed on said printed circuit board adjacent said camera.

5. The inspection apparatus of claim 4 wherein said printed circuit board is generally circular; wherein said light sources are a plurality of light emitting diodes disposed around the perimeter of said generally circular printed circuit board in order to form an illuminable ring substantially surrounding said camera.

6. The inspection apparatus of claim 1 wherein said flashlight assembly includes an electrical conductor and a switching apparatus, said electrical conductor being in electrical communication with said imaging system and said illumination assembly, said switching apparatus being operable between an ON position in which said electrical conductor is electrically, conductively connected to said power supply in order to provide power to said imaging system and said illumination assembly, and an OFF position in which said electrical conductor is not in electrical communication with said power supply.

7. The inspection apparatus of claim 1 wherein said power supply is a number of batteries disposed within said housing.

8. An inspection system for inspecting power generation equipment, said inspection system comprising:
  a remote receiving device adapted to receive images captured during inspection of said power generation equipment;
  a recording device structured to record said images; and
  an inspection apparatus for capturing said images, said inspection apparatus comprising:
    a flashlight assembly including a power supply, an elongated housing having a first end and a second end, a lens body coupled to the first end, and a lens cover covering said lens body, said lens body including an opening,
    an imaging system including a camera disposed within the opening of said lens body,
    an illumination assembly generally surrounding said camera said illumination assembly comprising a plurality of light sources; and
    a protective cover structured to at least partially overlay and to protect said illumination assembly, said protective cover including a center hole and a plurality of openings disposed around said center hole,
    wherein said camera extends through said center hole of said protective cover; and
    wherein each of said light sources extends through a corresponding one of said openings of said protective cover.

9. The inspection system of claim 8 wherein said camera is a wireless video camera; and wherein said imaging system comprises said wireless video camera and a transmitter which is adapted to transmit said images captured by said wireless video camera to said remote receiving device.

10. The inspection system of claim 9 wherein said transmitter is an RF transmitter; and wherein said remote receiving device is a RF receiver including an antenna which structured to receive said images transmitted from said RF transmitter.

11. The inspection system of claim 10 wherein said imaging system includes a display and a recording device, said display being in electrical communication with said remote receiving device in order to display said images captured by said wireless video camera; and wherein said recording device is structured to create a permanent record of said images.

12. The inspection system of claim 8 wherein said illumination assembly further comprises:
  a reflector disposed within said lens body;
  a printed circuit board coupled to said reflector and including an aperture, said camera being disposed within the aperture; and
  said light sources being disposed on said printed circuit board adjacent said camera.

13. The inspection system of claim 12 wherein said printed circuit board is generally circular; wherein said light sources are a plurality of light emitting diodes disposed around the perimeter of said generally circular printed circuit board in order to form an illuminable ring substantially surrounding said camera.

14. The inspection system of claim 8 wherein said flashlight assembly further includes an electrical conductor and a switching apparatus, said electrical conductor being in electrical communication with said imaging system and said illumination assembly, said switching apparatus being operable between an ON position in which said electrical conductor is electrically, conductively connected to said power supply in order to provide power to said imaging system and said illumination assembly, and an OFF position in which said electrical conductor is not in electrical communication with said power supply.

15. The inspection system of claim 8 wherein said power supply is a number of batteries disposed within said housing.

16. A method of inspecting power generation equipment, the method comprising:
  adapting a conventional flashlight to provide an inspection apparatus which comprises:
    a power supply,
    an elongated housing having a first end and a second end,
    a lens body coupled to the first end,
    a lens cover covering said lens body, said lens body including an opening,
    an imaging system including a camera disposed within the opening of said lens body,
    an illumination assembly generally surrounding said camera said illumination assembly comprising a plurality of light sources,
    a protective cover structured to at least partially overlay and to protect said illumination assembly, said protective cover including a center hole and a plurality of openings disposed around said center hole, and
    an electrical conductor with a switching apparatus, said electrical conductor being in electrical communication with said imaging system and said illumination assembly, said switching apparatus being operable between an ON position in which said electrical conductor is electrically, conductively connected to said power supply in order to provide power to said imaging system and said illumination assembly, and an OFF position in which said electrical conductor is not in electrical communication with said power supply,
    wherein said camera extends through said center hole of said protective cover; and
  wherein each of said light sources extends through a corresponding one of said openings of said protective cover.

17. The method of claim 16 further comprising:
  turning said switching apparatus of said inspection apparatus to said ON position in order to illuminate said illumination assembly and to begin capturing images with said imaging system; and conducting an inspection of said power generation equipment.

18. The method of claim 16 further comprising, providing as said imaging system a wireless video camera and a transmitter adapted to transmit said images captured by said wireless video camera to a remote receiving device.

19. The method of claim 18 further comprising:
providing as said transmitter a RF transmitter; and
providing as said remote receiving device a RF receiver including an antenna which is structured to receive said images transmitted from said RF transmitter.

20. The method of claim 18 further comprising:
providing said imaging system with a display and a recording device, said display being in electrical communication with said remote receiving device;
employing said inspection apparatus to conduct an inspection of said power generation equipment;
displaying on said display said images captured by said wireless video camera during said inspection; and
recording said images with said recording device.

* * * * *